United States Patent [19]

Yanagi et al.

[11] Patent Number: 4,666,507
[45] Date of Patent: May 19, 1987

[54] HERBICIDAL 5-HALO-1-[5-(N-SUBSTITUTED SULFONYLAMINO)PHENYL]PYRAZOLE DERIVATIVES

[75] Inventors: Mikio Yanagi, Ageo; Shuji Kawada, Yono; Fumio Futatsuya, Ohmiya; Kenji Kobayashi, Ageo, all of Japan

[73] Assignee: Nippon Kayaku Kabushiki Kaisha, Tokyo, Japan

[21] Appl. No.: 814,395

[22] Filed: Dec. 30, 1985

[30] Foreign Application Priority Data

Jan. 16, 1985 [JP] Japan .................................. 60-3957
Aug. 6, 1985 [JP] Japan ................................ 60-171793

[51] Int. Cl.⁴ .................. A01N 43/56; C07D 231/16; C07D 231/54
[52] U.S. Cl. ........................................ 71/92; 548/369; 548/375; 548/376
[58] Field of Search ...................... 548/369, 375, 376; 71/92

[56] References Cited

U.S. PATENT DOCUMENTS 4,008,249 2/1977 Fischer et al. ...................... 548/375
4,059,434 11/1977 Wolf .................................... 548/369

FOREIGN PATENT DOCUMENTS 52-91861 8/1977 Japan .................................. 548/375

Primary Examiner—John M. Ford
Assistant Examiner—Kurt G. Briscoe
Attorney, Agent, or Firm—Henry C. Nields

[57] ABSTRACT

Disclosed is a compound exhibiting herbicidal activity of the formula:

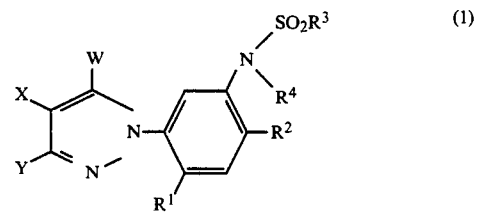

wherein $R^1$ is hydrogen, halogen or methyl, $R^2$ is hydrogen, halogen or lower alkyl, $R^3$ is lower alkyl which may be substituted by halogen or methylsulfonyl, benzyl or phenyl which may be substituted by halogen or nitro, $R^4$ is hydrogen; lower alkyl which may be substituted by carboxy or lower alkoxycarbonyl; lower alkenyl; lower alkynyl; methylsulfonyl or benzyl which may be substituted by halogen, X is hydrogen, halogen or $C_1$–$C_2$-alkyl, Y is $C_1$–$C_2$-alkyl, X may make —(CH$_2$)$_3$— or —(CH$_2$)$_4$— together with Y, W is halogen.

15 Claims, No Drawings

HERBICIDAL 5-HALO-1-[5-(N-SUBSTITUTED SULFONYLAMINO)PHENYL]PYRAZOLE DERIVATIVES

DETAILED DESCRIPTION OF THE INVENTION

This invention relates to a compound of the formula:

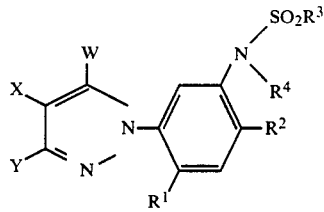

(1)

wherein
- $R^1$ is hydrogen, halogen or methyl,
- $R^2$ is hydrogen, halogen or lower alkyl,
- $R^3$ is lower alkyl which may be substituted by halogen or methylsulfonyl, benzyl or phenyl which may be substituted by halogen or nitro,
- $R^4$ is hydrogen; lower alkyl which may be substituted by carboxy or lower alkoxycarbonyl, lower alkenyl; lower alkynyl; methylsulfonyl or benzyl which may be substituted by halogen,
- X is hydrogen, halogen or $C_1$-$C_2$—alkyl,
- Y is $C_1$-$C_2$—alkyl,
- X may make —$(CH_2)_3$— or —$(CH_2)_4$— together with Y,
- W is halogen, a process for producing said compound, herbicidal composition containing said compound and a method for killing weeds comprising applying said compound to the weeds or locus thereof.

It has been known that some members of pyrazole derivatives have herbicidal activity (refer to the compounds disclosed in Japanese Patent Application Laid-Open No. 52-91861 (1977)).

These known pyrazole derivatives have never been effective at lower dosage to the harmful weeds in paddy fields and upland, and improved compounds have been desired.

As a result of the present inventors' studies on the various pyrazole derivatives, they have found that the compounds represented by the above formula (1) show an extremely strong herbicidal activity, and also can be utilized as a practical herbicide because of its little phytotoxicity to crop plants.

The novel pyrazole derivatives represented by the formula (1) according to the present invention can be produced, for instance, by the following process:

By reducing an N-substituted pyrazole represented by the formula (2):

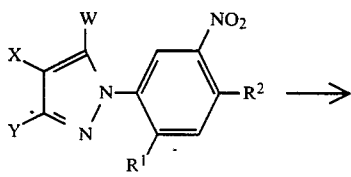

(2)

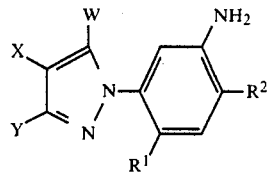

(3)

(wherein $R^1$, $R^2$, W, X and Y are respectively the meanings as given in the formula (1)), for instance by the usual reduction process of nitro- to amino-group an aromatic ring with sodium sulfide, iron powder, or catalytic reduction, a compound represented by the formula (3) (wherein $R^1$, $R^2$, W, X and Y are respectively the meanings as given in the formula (2)) can be obtained. The above-mentioned compounds represented by the formula (3) may be obtained, for instance, with iron powder in the presence of a catalytic amount of an acid such as hydrochloric acid in an aqueous alcohol solution, preferably at a temperature of 50° to 90° C. for 1 to 3 hours.

By reacting an N-substituted pyrazole represented by the formula (3):

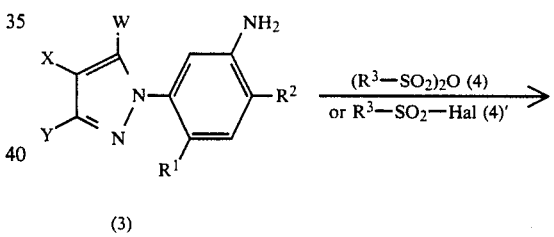

(3)

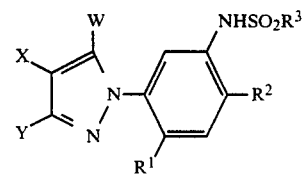

(5)

(wherein $R^1$, $R^2$, W, X and Y are respectively the meanings as given in the formula (2)) with a sulfonic anhydride or sulfonyl halide represented respectively by the formulae (4) or (4)' (wherein $R^3$ is the meanings as given in the formula (1) and Hal represents a halogen atom) preferably at a temperature of 0° to 50° C., occasionally in an inert solvent, if necessary, in the presence of a suitable basic catalyst, a pyrazole derivative represented by the formula (1) can be obtained.

By reacting an N-substituted pyrazole represented by the above-mentioned formula (5):

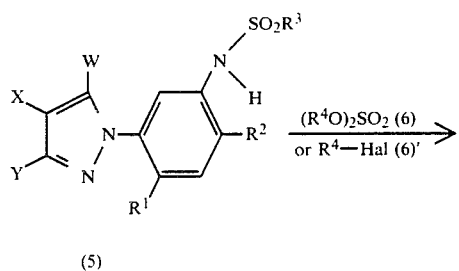

(5)

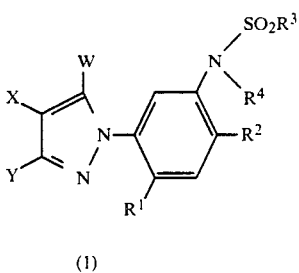

(1)

wherein $R^1$, $R^2$, $R^3$, W, X and Y are respectively the meanings as given in the formula (1) with a dialkyl sulfate or alkyl halide represented respectively by the formulae (6) or (6)′ (wherein $R^4$ represents lower alkyl which may be substituted by carboxy or carboxylic acid ester of lower alkyl; lower alkenyl; lower alkynyl; methylsulfonyl or benzyl which may be substituted by halogen and Hal represents halogen) preferably at a temperature of 20° to 100° C., if necessary, in the presence of a suitable basic catalyst, occasionally in an inert solvent, or alternatively, under a catalysis by a quaternary ammonium salt, preferably at a temperature of 20° to 100° C., with a suitable base in a water-inactive solvent, a pyrazole derivative represented by the formula (1) wherein $R^1$, $R^2$, $R^3$, $R^4$, W, X and Y are respectively the meanings as given above can be obtained.

By reacting a compound represented by the formula (7):

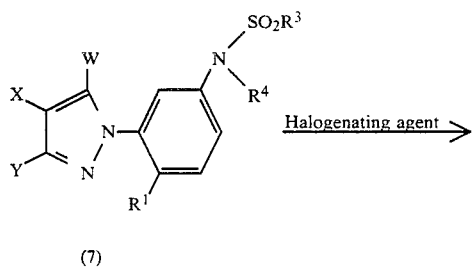

(7)

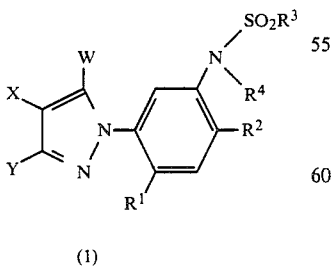

(1)

wherein $R^1$, $R^2$, $R^3$, $R^4$, W, X and Y are respectively the meanings as given above with a halogenating agent, preferably at a temperature of 0° to 80° C. for 1–5 hours with the optional addition of an inert solvent such as chloroform, methylene chloride, acetic acid and N,N-dimethyl formamide, a pyrazole derivative represented by the formula (1) (wherein $R^1$, $R^3$, $R^4$, W, X and Y are respectively the meanings as given above and $R^2$ represents a halogen atom), the pyrazole derivative can be obtained. As the halogenating agent, an ordinary reagent, preferably N-bromosuccinic imide, N-chlorosuccinic imide and sulfuryl chloride may be used.

A compound represented by the formula (2) (wherein $R^1$, $R^2$, W, X and Y are respectively the meanings as given above), used as a starting material is obtained by reacting an N-substituted pyrazolone represented by the formula (8):

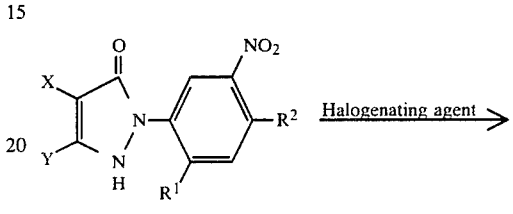

(8)

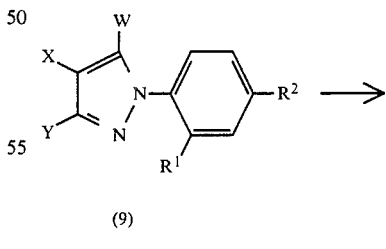

(2)

wherein $R^1$, $R^2$, X and Y are respectively the meanings as above with a halogenating agent, occasionally with the optional addition of an inert solvent such as chloroform, methylene chloride, or toluene, preferably at a temperature from 60° to 180° C. for 1 to 15 hours by heating. The above-mentioned reaction may be accelerated by the addition of a base such as dimethylformamide, pyridine or N,N-dialkylaniline. As the halogenating agent, an ordinary phosphorus halide, preferably phosphorus oxy-chloride or -bromide may be used.

By reacting an N-substituted pyrazole represented by the formula (9):

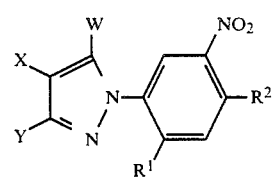

(9)

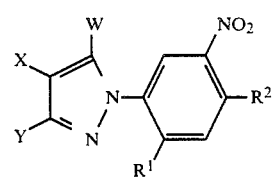

(2)

wherein $R^1$, $R^2$, W, X and Y are respectively the meanings as given in the formula (1) with a nitrating agent such as conc. nitric acid and fuming nitric acid preferably at a temperature of $-20°\text{-}30°$ C. in sulfuric acid, a compound represented by the formula (2) (wherein W, X, Y, $R^1$ and $R^2$ are respectively the same as above) can be obtained.

A compound represented by the formula (12) used as a starting material in the above-mentioned syntheses is obtained by bringing a compound represented by the formula (10) (wherein $R^5$ is a lower alkyl), and a substituted phenylhydrazine represented by the formula (11) (wherein $R^6$ is hydrogen atom or nitro group) into dehydration in a suitable inert solvent, for instance, an aliphatic hydrocarbon such as methylene chloride, or aromatic hydrocarbon such as toluene, alcohol or ethers, preferably at 60° to 150° C. for 30 min to 30 hours under reflux.

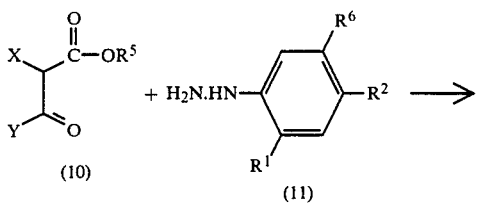

(10)  (11)

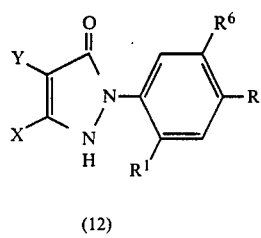

(12)

In the above-mentioned reaction, if necessary, the reaction can be completed under milder conditions, for example, at 5° C. to temperature of reflux, by the addition of a suitable base, for instance, triethylamine, sodium hydroxide and alcoholates.

A substituted phenylhydrazine represented by the formula (11) can be obtained by diazotizing a substituted aniline represented by the following formula (13) (wherein $R^1$ and $R^2$ are respectively the meanings as above), with sodium nitrite, and reducing the diazonium salt thus obtained with a reducing agent such as stannous chloride or sodium hydrogen sulfite.

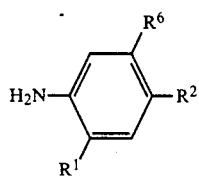

(13)

A compound represented by the formula (15) (wherein X is a halogen and Y, W, $R^1$, $R^2$ and $R^7$ are respectively the meanings as above and $R^7$ is hydrogen, nitro or

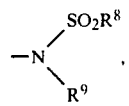

$R^8$ and $R^9$ are lower alkyl) can be obtained by halogenating a compound represented by the formula (14) (wherein Y, W, $R^1$, $R^2$ and $R^7$ are respectively the meanings as given above), in acetic acid or an inert solvent such as chloroform etc., preferably at 0° to 30° C., using a halogenating agent such as chlorine or bromine.

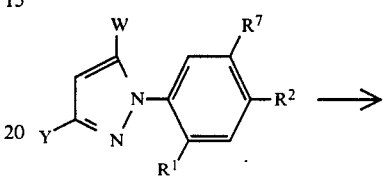

(14)

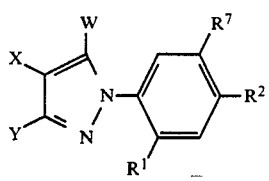

(15)

As the basic catalyst according to the present invention, triethylamine, tributylamine, pyridine, N-methylmorpholine, N,N-diethylaniline, N,N-dimethylaniline, potassium and sodium carbonates may be mentioned.

As the inert solvent according to the present invention, an aromatic hydrocarbon such as benzene, toluene and xylene and a halogen derivative thereof such as chlorobenzene, an aliphatic hydrocarbon such as n-hexane, n-heptane and petroleum ether, a cycloaliphatic hydrocarbon such as cyclohexane, a halogenated aliphatic hydrocarbon such as chloroform, carbon tetrachloride and tetrachloroethylene, an ether such as ethyl ether, tetrahydrofuran and dioxane, as ester such as ethyl acetate, an amide such as dimethylformamide and water may be mentioned.

According to the present invention, as the halogen atom, a chlorine atom, a bromine atom or a fluorine atom may be mentioned, and as the lower alkyl group, methyl, ethyl, n- and iso-propyl groups may be mentioned. Also, as the halogen- or nitro-substituted phenyl group, p-nitrophenyl, m-nitrophenyl, p-chlorophenyl, m-chlorophenyl and 2-chloro-4-nitrophenyl groups may be mentioned, and as the lower alkyl group substituted or carboxy or carboxylic acid ester of lower alkyl group, $-CH_2COOCH_3$, $-CH_2COOC_2H_5$ etc. may be mentioned. As the lower alkenyl group, $-CH_2-CH=CH_2$ and

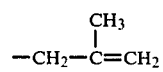

may be mentioned and as the lower alkynyl group, $-CH_2C\equiv CH$ may be mentioned.

Of the present compounds, the preferable ones represented by the following groups (A) and (B) may be mentioned: (A): A compound of the formula (1) wherein $R^1$ is fluoro or chloro, $R^2$ is chloro or methyl, $R^3$ is lower alkyl, $R^4$ is methyl, ethyl, carboxymethyl or methoxy carbonyl methyl, X is chloro, Y is methyl or X makes —$(CH_2)_4$— together with Y and W is chloro. (B): A compound according to claim 1 wherein $R^1$ is fluoro, chloro or methyl, $R^2$ is chloro, bromo or methyl, $R^3$ is —$SO_2CF_3$, $R^4$ is hydrogen, X is methyl or X makes —$(CH_2)_4$— together with Y, and the more preferable ones are those represented by a compound wherein $R^1$ is fluoro, $R^2$ is chloro, $R^3$ is methyl or ethyl, $R^4$ is methyl, carboxymethyl or methoxycarbonylmethyl, X is chloro, Y is methyl or X makes —$(CH_2)_4$— together with Y, W is chloro, and in addition, the most preferable compounds are the compounds represented by the formula:

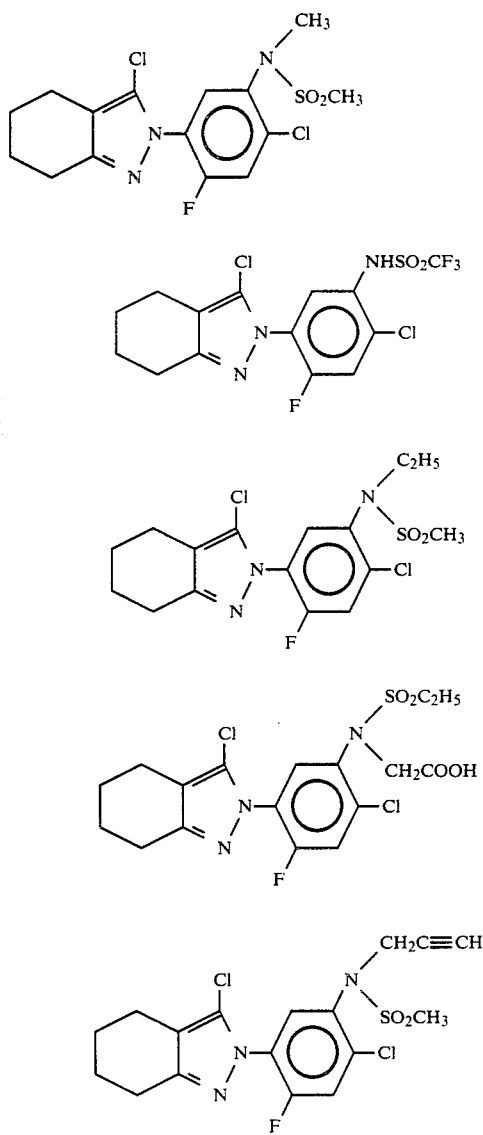

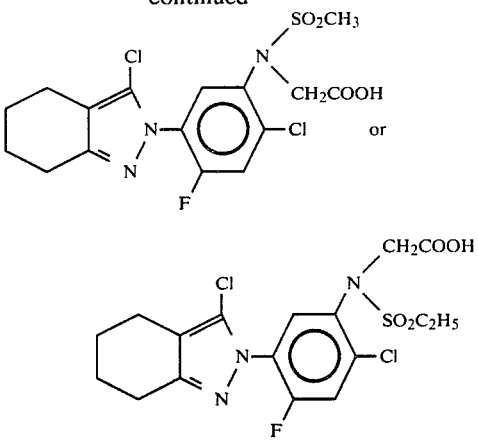

When the compound of the present invention is used for a herbicidal composition, according to the purpose of promoting or stabilizing the effect thereof, it may be used in the form of formulation such as dust, granule, micro granule, emulsifiable concentrate, wettable powder, flowable suspension concentrate by mixing with adjuvants in a conventional method of the agrochemical manufacture.

The various formulations may be used on actual application such or after being diluted to a desirable concentration by water.

As the adjuvants, carriers (diluents) and other adjuvants, for instance, extenders, emulsifiers, wetting agents, dispersing agents, fixing agents and disintegrators may be mentioned.

Namely, as a liquid carrier, aromatic hydrocarbons such as toluene, xylene and methylnaphthalene, aliphatic hydrocarbons such as cyclohexane, ligroin and kerosene, alcohols such as methanol, butanol and glycol, ketones such as acetone, amides such as dimethylformamide, sulfoxides such as dimethylsulfoxide, animal and vegetable oils, fatty acids and esters thereof may be mentioned. As a solid carrier, clay, kaolin, talc, diatomaceous earth, silica, calcium carbonate, montmorillonite, bentonite, feldspar, quartz, alumina and sawdust may be mentioned.

As an emulsifier or a dispersing agent, usually a surfactant is used, for instance, an anionic surfactant such as sodium higher alkyl sulfate, stearyl-trimethylammonium chloride, polyoxyethylene alkylphenyl ether and laurylbetain, a cationic surfactant, a non-ionic surfactant and an amphoteric surfactant may be mentioned. As an extender, for instance, polyoxyethylene nonylphenyl ether and polyoxyethylene lauryl ether may be mentioned, and as a wetting agent, for instance, dialkyl sulfosuccinate and polyoxyethylene nonylphenyl ether may be mentioned. As a fixing agent, carboxymethylcellulose and polyvinyl alcohol may be mentioned, and as a disintegrator, sodium ligroinsulfonate and calcium salt of carboxymethylcellulose may be mentioned.

Every herbicidal composition mentioned above can be used not only alone but in combination with fungicides, insecticides, acaricides, nematocides, plant growth regulators or soil improving agents. In addition, the herbicidal composition according to the present invention can be used after mixing with any fertilizers and other herbicides.

The content of the active compound in the herbicidal composition according to the present invention depends on the type and form of formulation, the method of application and other conditions, and the content of the present compound is in a range from 0.1 to 95% by weight, preferably from 0.5 to 50% by weight.

When weed-control is carried out, the amount of application of the herbicidal composition depends on the present compound used in the herbicidal composition and the fields to which the herbicidal composition is applied, however, in general, 0.1 g, preferably 20 g of one of the present compound is applied per one are (1 are = 100 m$^2$) of the field.

The compounds according to the present invention show an excellent herbicidal activity at a low concentration to arrowhead, bulrush, and mizugayatsuri in paddy fields with very little phytotoxicity to rice and also show an excellent activity at a low concentration to crabgrass, foxtail, wild amaranth and lamb's quarters with little toxicity to the crop plant such as maize, soy bean and cotton in up-land.

The present invention is further illustrated by the following examples.

SYNTHETIC EXAMPLE 1

1-(3-Trifluoromethylsulfonylamino-4-chlorophenyl)-3,4-tetramethylene-5-chloropyrazole (compound No. 3):

Into 20 ml of methylene chloride, 1.5 g (0.0053 mol) of 1-(3-amino-4-chlorophenyl)-3,4-tetramethylene-5-chloropyrazole (reference No. 6) were dissolved, and 1.7 g (0.0060 mol) of trifluoromethane-sulfonic anhydride were added to the solution at −5° to 0° C., and then 0.6 g (0.0059 mol) of triethylamine were added. After stirring the solution for 2 hours at the same temperature, the whole solution were poured into water, and the dichloromethane layer was extracted with a 5% aqueous solution of sodium hydroxide. The alkaline extracts were acidified by hydrochloric acid and were extracted with ethyl acetate. By washing out the ethyl acetate layer with water, drying and concentrating, 1.1 g of a yellow crystal were obtained. (yield 50%), melting point: 180° to 184° C.

Elementary analysis $C_{14}H_{12}Cl_2F_3N_3O_2S$ (414.25) Calcd. C: 40.59, H: 2.93, N: 10.15; Found C: 40.15, H: 2.90, N: 10.18.

SYNTHETIC EXAMPLE 2

1-(2-fluoro-4-chloro-5-trifluoromethanesulfonylaminophenyl)-3,4-tetramethylene-5-chloropyrazole (compound No. 7):

3.5 g (0.012 mol) of 1-(2-fluoro-4-chloro-5-aminophenyl)-3,4-tetramethylene-5-chloropyrazole were dissolved in 20 ml of methylene chloride, and after the solution were ice-cooled, 1.7 ml (0.12 mol) of triethylamine were added into the solution and 2.1 ml (0.12 mol) of trifluoromethanesulfonic anhydride were added dropwise. After stirring for 1 hour, the reaction mixture was poured into water, and extracted with ethyl acetate. After washing with water and concentrating, the extract was separated and purified in a silica gel column and 3.9 g of the desired product were obtained as a yellow crystal (yield 75%), melting point 199° to 202° C.

Elementary analysis $C_{14}H_{11}Cl_2F_2N_3O_2S_1$ Calcd. C: 38.90, H: 2.57, N: 9.72; Found C: 38.95, H: 2.65, N: 9.76.

SYNTHETIC EXAMPLE 3

1-(4-Chloro-2-fluoro-5-methanesulfonylaminophenyl)-3,4-tetramethylene-5-chloropyrazole (compound No. 16):

2 g of 1-(5-amino-4-chloro-2-fluorophenyl)-3,4-tetramethylene-5-chloropyrazole were mixed with 5 ml of pyridine and after cooling to 0° C., 0.86 g of methanesulfonyl chloride were added dropwise therein while stirring.

After stirring for 2 hours, the reaction mixture was poured into water, extracted with ethyl acetate and washed with dilute hydrochloric acid. After further washing with dilute aqueous sodium bicarbonate solution and ice water, the extract was dried over anhydrous sodium sulfate and recrystallized from the mixed solvent of n-hexane-ethyl acetate to obtain 2.0 g of white crystals, melting point: 175° C. 176° C. (yield 80%).

Elementary analysis: $C_{14}H_{14}Cl_2F_1N_3O_2S_1$ Calcd: C: 44.46, H: 3.73, N: 11.11; Found: C: 44.51, H: 3.69, N: 11.30.

SYNTHETIC EXAMPLE 4

1-[4-Chloro-2-fluoro-5-(N-methyl-N-methanesulfonyl)aminophenyl]-3,4-tetramethylene-5-chloropyrazole (compound No. 14)

1.6 g of 1-(4-chloro-2-fluoro-5-methanesulfonylaminophenyl)-3,4-tetramethylene-5-chloropyrazole (compound No. 16) were dissolved in 40 ml of acetonitrile, added with 0.6 g of dimethyl sulfate and 0.64 g of potassium carbonate, and stirred for 3 hours under reflux. After cooling, the reaction mixture was poured in water, extracted with ethyl acetate and washed with water to neutral. Subsequently concentrated, isolated and purified on silica-gel column chromatography, 1.3 g of white crystals were obtained, melting point 78° to 81° C. (yield 85.5%)

Elementary analysis: $C_{15}H_{16}Cl_2F_1N_3O_2S_1$ Calcd.: C: 45.93, H: 4.11, N: 10.71; Found: C: 46.04, H: 4.06, N: 10.82.

SYNTHETIC EXAMPLE 5

1-[4-Chloro-2-fluoro-5-(N-ethylsulfonyl-N-methoxycarbonylmethyl)aminophenyl]-3,4-tetramethylene-5-chloropyrazole (compound No. 35):

3.8 g of 1-(4-chloro-2-fluoro-5-ethanesulfonylaminophenyl)-3,4-tetramethylene-5-chloropyrazole (compound No. 19) were dissolved in 50 ml of acetonitrile, and added thereto with 1.8 g of methyl α-bromoacetate and 1.7 g of potassium carbonate. After stirred for 3 hours under reflux, cooled and poured into water, the reaction mixture was extracted with ethyl acetate, washed with water to neutral and after concentrating isolated and purified on silica-gel column chromatography to obtain 3.2 g of white crystals, melting point: 134.5° to 135.5° C. (yield 71%)

Elementary analysis: $C_{18}H_{20}Cl_2F_1N_3O_4S_1$ Calcd.: C: 46.56, H: 4.34, N: 9.05; Found: C: 46.72, H: 4.45, N: 9.10.

SYNTHETIC EXAMPLE 6

1-[4-Chloro-2-fluoro-5-(N-propargyl-N-methanesulfonyl)-aminophenyl]-3,4-tetramethylene-5-chloropyrazole (compound No. 29)

1.9 g of 1-(4-chloro-2-fluoro-5-methanesulfonylaminophenyl)-3,4-tetramethylene were dissolved in 50 ml of acetonitrile. 1.3 g of propargyl bromide and 1.5 g of potassium carbonate were added thereto and after stirring for 4 hours under reflux, the reaction mixture was cooled, poured in water and extracted with ethyl acetate. The extract was washed with water to neutral, concentrated and thereafter under separation and purification on silica-gel column chromatography, 1.7 g of white crystals, melting at 136°–137° C. (yield 81%).

Elementary analysis $C_{17}H_{16}Cl_2F_1N_3O_2S_1$ Calcd.: C: 49.05, H: 3.87, N: 10.09; Found: C: 48.96, H: 3.74, N: 10.18.

SYNTHETIC EXAMPLE 7

1-[4-Chloro-2-fluoro-5-(N,N-dimethanesulphonyl)aminophenyl]-3-methyl-4,5-dichoropyrazole (compound No. 24)

2.0 g of 1-(5-amino-4-chloro-2-fluorophenyl)-3-methyl-4,5-dichloro were dissolved in 30 ml of methylene and added with 1.7 g of methanesulfonyl chloride dropwise. With further addition 2 ml of triethylamine, the reaction mixture was stirred for 3 hours at room temperature, poured into water, extracted with ethyl acetate and washed by water. The concentrated product was isolated and purified on silica-gel column chromatography to obtain 1.7 g of pale brown crystals, melting point: 190° to 192° C. (yield 65.4%)

Elementary analysis: $C_{12}H_{11}Cl_2F_1N_3O_4S_2$ Calcd.: C: 31.98, H: 2.46, N: 9.32; Found: C: 31.90, H: 2.53, N: 9.44.

SYNTHETIC EXAMPLE 8

1-[4-Chloro-2-fluoro-5-(N-methyl-N-methanesulfonyl)-aminophenyl]-3,4-tetramethylene-5-chloropyrazole Compound No. 14)

3 g of 1-[2-fluoro-5-(N-methyl-N-methanesulfonylamino)phenyl]-3,4-tetramethylene-5-chloropyrazole, 1.3 g of sulfuryl chloride and 30 ml of carbon tetrachloride were mixed and stirred for 6 hours at 70° C. The mixture was poured in water and washed with dilute aqueous sodium bicarbonate and further water. The product was dried, concentrated and recrystallized from the solvent mixture of n-hexane-ethyl acetate to obtain 2.8 g of white crystal, melting point: 78° to 81° C. (yield 85%).

Elementary analysis: $C_{15}H_{16}Cl_2F_1N_3O_2S_1$ Calcd.: C: 45.92, H: 4.12, N: 10.71; Found: C: 45.99, H: 4.11, N: 10.69.

REFERENCE EXAMPLE 1

Synthesis of 1-(4-chloro-2-fluorophenyl)-3-methyl-5-chloropyrazole:

21.8 g (0.136 mol) of 4-chloro-2-fluorophenyl hydrazine and 18.5 g (0.142 mol) of ethyl 3-oxobutanoate were dissolved in toluene, and the solution was heated under reflux, then concentrated. A small amount of ether was added to the solution, and the precipitated crystals were filtrated to obtain 26.1 g of 1-(4-chloro-2-fluorophenyl)-2H-3-methyl-5-pyrazolone in yield of 85%. To the obtained red crystals, 15.3 g (0.126 mol) of N,N-dimethylaniline and 19.4 g (0.126 mol) of phosphorus oxychloride were added and, after heated to 130° C., stirred for 5 hours. The reaction mixture was poured in ice water and extracted with chloroform. The chloroform layer was washed with a dilute hydrochloric acid, followed by water. The solid matter obtained by concentrating of the extract was purified on column chromatography to obtain 15.0 g of 1-(4-chloro-2-fluorophenyl)-3-methyl-5-chloropyrazole as a pale yellow crystal, melting point: 95° to 97° C. in yield of 53%.

REFERENCE EXAMPLE 2

Synthesis of 1-(4-chloro-2-fluoro-5-nitrophenyl)-3-methyl-4-bromo-5-chloropyrazole:

The solution of 12.5 g (0.043 mol) of 1-(4-chloro-2-fluoro-5-nitrophenyl)-3-methyl-5-chloropyrazole in the mixed solvent made of 100 ml of chloroform and 100 ml of acetic acid was added with 3.9 g (0.047 mol) of sodium acetate, followed by 7.2 g (0.045 mol) of bromine at 10° C. After stirred at the same temperature for 2 hours, the reaction mixture was poured into ice water and the chloroform layer was separated. The chloroform layer was washed with an aqueous sodium bicarbonate and water and concentrated to obtain 13.0 g of 1-(4-chloro-2-fluoro-5-nitrophenyl)-3-methyl-4-bromo-5-chloropyrazole as pale yellow crystals, melting point: 135° to 137° C. in yield of 82%.

REFERENCE EXAMPLE 3

Synthesis of 1-(4-chloro-2-fluoro-5-nitrophenyl)-3,4-tetramethylene-5-chloropyrazole:

8.7 g (0.0305 mol) of 1-(4-chloro-2-fluorophenyl)-3,4-tetramethylene-5-chloropyrazole were added to 20 ml of concentrated sulfuric acid, and under cooling, 1.64 ml (0.335 mmol) of fuming nitric acid (d=1.5, p. 86%) were dropped dropwise. After a while stirring, the reaction mixture was poured into a great amount of water, and after extracting with ethyl acetate, the extract was separated and purified on silica-gel column chromatography to obtain 8.2 g of the object product as brown crystals, melting point: 108° to 111° C., in yield of 82%.

REFERENCE EXAMPLE 4

Synthesis of 1-(4-chloro-3-nitrophenyl)-3,4-tetramethylene-5-chloropyrazole:

9.5 g (0.056 mol) of ethyl 2-oxocyclohexanoate and 7.9 g (0.055 mol) of 4-chlorophenylhydrazine were dissolved in 50 ml of xylene, and after heating the solution for 3 hours under reflux, the crystal-formed by concentrating the mixture was filtered to obtain 12.8 g of 1-(4-chlorophenyl)-2H-3,4-tetramethylene-5-pyrazolone.

To the whole amount of the obtained crystal, 8.7 g of phosphorus oxychloride and 6.9 g of N,N-dimethylaniline were added and, after stirring for 5 hours at 130° C., the reaction mixture was poured to ice water, followed by extraction with chloroform. The chloroform layer was washed with a dilute hydrochloric acid and water and then the solid substance obtained by concentration was purified on column chromatography to obtain 10 g of 1-(4-chlorophenyl)-3,4-tetramethylene-5-chloropyrazole as pale yellow crystals in yield of 73%.

6.0 g (0.022 mol) of the 1-(4-chlorophenyl)-3,4-tetramethylene-5-chloropyrazole thus obtained were dissolved in 20 ml of concentrated sulfuric acid and added with 2.3 g of concentrated nitric acid (94%) at −5° to 0° C. After stirring for 2 hours at the same temperature, the reaction mixture was poured into ice water, neutralized with NaHCO₃ and extracted with ethyl acetate. The concentrate was purified on column chromatography to obtain 5.3 g of the object product as yellow crystls, melting point: 94° to 97° C., in yield of 76%.

REFERENCE EXAMPLE 5

Synthesis of 1-(5-amino-4-chloro-2-fluorophenyl)-3-methyl-4-bromo-5-chloropyrazole:

12.5 g (0.034 mol) of 1-(4-chloro-2-fluoro-5-nitrophenyl)-3-methyl-4-bromo-5-chloropyrazole (reference example 2) were added in the solution of 13.6 g of iron powder, 44 ml of ethanol, 20 ml of water and 0.2 ml of hydrochloric acid at 70° to 75° C., under stirring. After stirred for 2 hours at 75° C., the reaction mixture was filtered and the filtrate added with cold water was extracted with ethyl acetate. The ester layer was washed with water, concentrated and purified on column chromatography to obtain 11.0 g of brown crystal, melting point: 113° to 116° C. in yield of 96%.

REFERENCE EXAMPLE 6

Synthesis of 1-(3-amino-4-chlorophenyl)-3,4-tetramethylene-5-chloropyrazole:

p 4.5 g (0.014 mol) of 1-(4-chloro-3-nitrophenyl)-3,4-tetramethylene-5-chloropyrazole (reference example 5) were added to the solution of 5.8 g of iron powder, 20 ml of ethanol, 9 ml of water and 0.1 ml of hydrochloric acid at 70° to 75° C. under stirring. After stirred for 2 hours at 75° C., the reaction mixture was filtered and the filtrate added with cold water was extracted with ethyl acetate. The ester layer was washed with water, concentrated and purified on column chromatography to obtain 3.2 g of brown crystal, melting point: 87° to 89° C., in yield of 79%.

The present compounds represented by the formula (1) are summarized in the following Table 1:

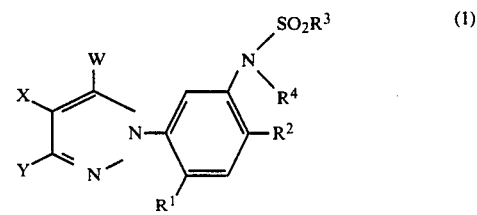

(1)

TABLE 1

| Compound No. | X | Y | W | R₁ | R₂ | R₃ | R₄ | m.p.; $n_D^{25}$ | Appearance |
|---|---|---|---|---|---|---|---|---|---|
| 1 | —(CH₂)₄— | | Cl | CH₃ | CH₃ | CF₃ | H | 195–7° C. | white crystal |
| 2 | CH₃ | CH₃ | " | F | Cl | " | " | 190–2° C. | brown crystal |
| 3 | —(CH₂)₄— | | " | H | Cl | " | " | 180–4° C. | yellow crystal |
| 4 | " | | " | CH₃ | CH₃ | " | " | 138–41° C. | pale yellow crystal |
| 5 | " | | " | H | CH₃ | " | " | 161–3° C. | " |
| 6 | " | | " | H | C₂H₅ | " | " | 193–6° C. | " |
| 7 | " | | " | F | Cl | " | " | 199–202° C. | " |
| 8 | " | | " | H | H | " | " | 199–200° C. | " |
| 9 | H | CH₃ | " | F | Cl | " | " | 183–6° C. | brown crystal |
| 10 | Br | CH₃ | " | " | " | " | " | 175–7° C. | " |
| 11 | —(CH₂)₄— | | " | " | Br | " | " | 200–1.5° C. | pale brown crystal |
| 12 | Cl | CH₃ | " | " | Cl | C₂H₅ | " | 130–2° C. | pale yellow crystal |
| 13 | " | " | " | " | " | " | CH₃ | 141–2° C. | " |
| 14 | —(CH₂)₄— | | " | " | " | CH₃ | " | 78–81° C. | white crystal |
| 15 | " | | " | " | " | " | C₂H₅ | 109–111° C. | " |
| 16 | " | | " | " | " | " | H | 175–6° C. | " |
| 17 | " | | " | " | " | C₂H₅ | " | 139–40° C. | pale brown crystal |
| 18 | " | | " | H | " | CH₃ | " | 144–5° C. | white crystal |
| 19 | " | | " | H | " | C₂H₅ | " | 124–6° C. | pale brown crystal |
| 20 | Cl | CH₃ | " | F | " | CH₃ | CH₃ | 40–3° C. | pale yellow crystal |
| 21 | —(CH₂)₄— | | " | " | " | CH₂Cl | H | 182–3° C. | pale brown crystal |
| 22 | " | | " | " | " | C₃H₇(n) | " | glassy | pale yellow glass |
| 23 | Cl | CH₃ | " | " | " | CH₃ | " | 43–5° C. | " |
| 24 | " | " | " | " | " | " | SO₂CH₃ | 190–2° C. | pale brown crystal |
| 25 | Br | " | " | " | " | " 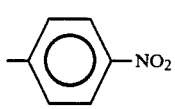 | H | 230–3° C. | pale yellow crystal |
| 26 | —(CH₂)₄— | | " | H | CH₃ | 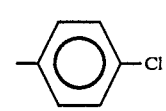 | " | 153–4° C. | white crystal |
| 27 | " | " | " | F | Cl | 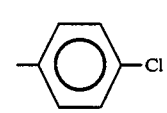 | " | 190–2° C. | " |
| 28 | " | " | " | CH₃ | CH₃ | CH₃ | " | 194–6° C. | pale yellow crystal |
| 29 | " | " | " | F | Cl | " | —CH₂C≡CH | 136–7° C. | white crystal |
| 30 | " | " | " | " | " | " | —CH₂—CH=CH₂ | 103–5° C. | " |
| 31 | " | " | " | " | " | " | —C₃H₇(i) | 86–8° C. | white crystal |

TABLE 1-continued

| Compound No. | X | Y | W | $R_1$ | $R_2$ | $R_3$ | $R_4$ | m.p.; $n_D^{25}$ | Appearance |
|---|---|---|---|---|---|---|---|---|---|
| 32 | " | " | " | " | " | 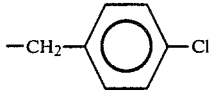 | | 58–62° C. | " |
| 33 | " | " | " | " | " | 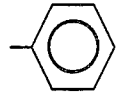 | H | 174–5° C. | pale brown crystal |
| 34 | " | " | " | " | " | 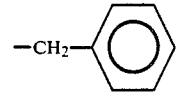 | " | 172–3° C. | white crystal |
| 35 | " | " | " | " | " | —$C_2H_5$ | —$CH_2COOCH_3$ | 134.5–5.5° C. | " |
| 36 | " | " | " | " | " | " | —$CH_2COOH$ | 238–9° C. | " |
| 37 | " | " | " | F | " | —$CH_3$ | H | 212–4° C. | " |
| 38 | " | " | H | Cl | " | " | $CH_3$ | 99–101° C. | " |
| 39 | " | " | F | " | " | —$CH_2Cl$ | " | 1.5755 | pale yellow oil |
| 40 | " | " | H | $CH_3$ | " | $CH_3$ | H | 128–30° C. | white crystal |
| 41 | " | " | " | " | " | " | $CH_3$ | 105–7° C. | " |
| 42 | " | " | F | Br | " | " | H | 175.5–7° C. | pale yellow crystal |
| 43 | " | " | " | " | " | " | $CH_3$ | | pale yellow glass |
| 44 | " | " | Cl | Cl | " | " | H | 200–2° C. | pale yellow crystal |
| 45 | " | " | " | " | " | " | $CH_3$ | 64–6° C. | " |
| 46 | " | " | F | Br | " | " | $SO_2CH_3$ | 198–9° C. | white crystal |
| 47 | " | " | " | " | $CH_3$ | " | H | | |
| 48 | " | " | " | " | " | " | $CH_3$ | | |
| 49 | Cl | $CH_3$ | " | " | Cl | $CH_2SO_2CH_3$ | $CH_3$ | 123–5° C. | white crystal |
| 50 | —$(CH_2)_4$— | | " | H | H | $CH_3$ | H | 176–8° C. | pale yellow crystal |
| 51 | " | | " | " | " | " | $CH_3$ | 132–3° C. | white crystal |
| 52 | " | | " | " | $C_2H_5$ | " | H | 146–7° C. | pale brown crystal |
| 53 | " | | " | " | " | " | $CH_3$ | 148–9° C. | " |
| 54 | " | | " | F | Cl | $C_2H_5$ | " | 45–49° C. | " |
| 55 | " | | " | " | " | $C_3H_7(n)$ | " | glassy | brown glassy |
| 56 | " | | " | " | " | Bu (n) | H | 102–4° C. | brown crystal |
| 57 | " | | " | " | " | " | $CH_3$ | 38–42° C. | pale brown crystal |
| 58 | " | | " | " | " | 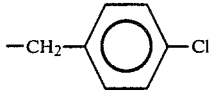 | " | 131–2° C. | white crystal |
| 59 | " | | " | " | " | 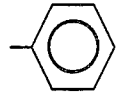 | " | 143–4° C. | pale brown crystal |
| 60 | " | " | " | " | F | $CH_3$ | " | | |
| 61 | " | " | " | " | H | " | H | 147.5–9° C. | " |
| 62 | " | " | " | " | " | " | $CH_3$ | 144.5–5.5° C. | " |
| 63 | Cl | $CH_3$ | " | " | Cl | " | H | 130–2° C. | " |
| 64 | " | " | " | " | " | " | $CH_3$ | 141–3° C. | " |

The herbicidal composition of the present invention is explained more in detail, while the kind and composition of the ingredients may be applicable to wider extent than the descriptions in following examples. Parts means "parts by weight" in the examples.

FORMULATION EXAMPLE 1

Emulsifiable concentration

Into 35 parts of xylene, 50 parts of the present compound No. 3 were dissolved, and the thus formed solution was mixed with 15 parts of a mixture (8:2) of polyoxyethylene alkylphenylether and calcium alkylbenzenesulfonate to obtain an emulsifiable concentration. In application, the thus formulated composition is diluted with water, thereby obtaining an aqueous emulsion containing 0.01 to 1% of the present compound No. 3.

FORMULATION EXAMPLE 2

Dust

To 95 parts of clay, 5 parts of the present compound No. 9 were added, and by blending and pulverizing the mixture, a dust was obtained. It is directly applicable onto the ground where the weeds are grown, or are expected to grow.

FORMULATION EXAMPLE 3

Wettable powder

A mixture of 50 parts of the present compound No. 18, 10 parts of diatomaceous earth and 32 parts of kaolin was blended with 8 parts of a mixture (1:1) of sodium laurylsulfate and sodium 2,2'-dinaphthylmethanesulfonate, and by pulverizing the mixture, a wettable powder was obtained.

In application of the thus obtained composition, it is diluted with water to be an aqueous suspension containing 0.06 to 1% of the present compound No. 18.

FORMULATION EXAMPLE 4

Granule

5 Parts of a fine dust of compound No. 6 were extended for coating on 94.5 parts of grains (16 to 32 mesh) of silica to obtain a granule, by using a methanol solution of 0.5 parts of polyvinyl acetate as a binding agent in a proper mixer. The granule is scattered directly in paddy fields.

TEST EXAMPLE 1

Pre-emergence treatment in flooded condition

A fixed amount of paddy field soil was filled in each Wagner pot sized 1/5,000 are to provide a condition similar to a paddy field and their was sown a fixed amount of seeds of barnyard grass, monochloria, toothcup, false pimpernal, water wort and bulrush.

In addition, tubers of arrowhead were buried 1 cm under the surface of soil at the rate of 3 pieces per pot and the pot was flooded with water 3 cm deep. Then the pot was applied with a dilute solution of the compound of the present invention at a rate of 0.8 to 50 g of the active compound of the present invention per are. After 3 days 3 pieces of rice seedlings (variety: Nihonbare) in 2.5-leaf stage were transplanted from a nursery to each pot. Thirty days after the treatment the herbicidal activity and the phytotoxicity against paddy rice were observed. The test results were classified on the following basis as shown in Table 2.

Herbicidal activity index:
5: complete weeding
4: up to 80% weeding
3: up to 60% weeding
2: up to 40% weeding
1: up to 20% weeding
0: no effect Phytotoxicity index:
−: no damage
+: slight damage
++: some damage
+++: moderate damage
++++: heavy damage
X: complete death

TABLE 2

| | | Pre-emergence treatment under flooded condition | | | | |
|---|---|---|---|---|---|---|
| | | Herbicidal activity | | | | Phyto- |
| Compound No. | Dosage g/a | barnyard grass | broad-leaf(1) | allow-head | bulruch | toxicity to rice |
| 1 | 0.8 | 5 | 5 | 2 | 1 | − |
| | 3.1 | 5 | 5 | 5 | 5 | − |
| | 12.5 | 5 | 5 | 5 | 5 | − |
| 2 | 3.1 | 2 | 5 | 4 | 4 | − |
| | 12.5 | 4 | 5 | 5 | 5 | + |
| | 50 | 5 | 5 | 5 | 5 | ++ |
| 3 | 0.8 | 5 | 5 | 4.5 | 5 | − |
| | 3.1 | 5 | 5 | 5 | 5 | − |
| | 12.5 | 5 | 5 | 5 | 5 | − |
| 5 | 0.8 | 5 | 5 | 3 | 3 | − |
| | 3.1 | 5 | 5 | 5 | 5 | − |
| | 12.5 | 5 | 5 | 5 | 5 | − |
| 6 | 0.8 | 5 | 5 | 3 | 3 | − |
| | 3.1 | 5 | 5 | 5 | 5 | − |
| | 12.5 | 5 | 5 | 5 | 5 | − |

TABLE 2-continued

| | | Pre-emergence treatment under flooded condition | | | | |
|---|---|---|---|---|---|---|
| | | Herbicidal activity | | | | Phyto- |
| Compound No. | Dosage g/a | barnyard grass | broad-leaf(1) | allow-head | bulruch | toxicity to rice |
| 7 | 0.8 | 5 | 5 | 5 | 5 | − |
| | 3.1 | 5 | 5 | 5 | 5 | − |
| | 12.5 | 5 | 5 | 5 | 5 | − |
| standard CNP | 3.1 | 0 | 5 | 0 | 0 | − |
| | 12.5 | 4 | 5 | 0 | 0 | − |
| not treated | — | 0 | 0 | 0 | 0 | − |
| 13 | 0.8 | 5 | 5 | 5 | 5 | − |
| | 3.2 | 5 | 5 | 5 | 5 | − |
| 14 | 0.8 | 5 | 5 | 5 | 5 | − |
| | 3.2 | 5 | 5 | 5 | 5 | − |
| 15 | 0.8 | 5 | 5 | 5 | 4 | − |
| | 3.2 | 5 | 5 | 5 | 5 | + |
| 16 | 0.8 | 5 | 5 | 3 | 5 | − |
| | 3.2 | 5 | 5 | 5 | 5 | + |
| 17 | 0.8 | 5 | 5 | 2 | 5 | − |
| | 3.2 | 5 | 5 | 5 | 5 | − |
| 19 | 0.8 | 5 | 5 | 1 | 3 | − |
| | 3.2 | 5 | 5 | 2 | 5 | − |
| 21 | 0.8 | 5 | 5 | 3 | 5 | − |
| | 3.2 | 5 | 5 | 5 | 5 | − |
| 22 | 0.8 | 5 | 5 | 3 | 4 | − |
| | 3.2 | 5 | 5 | 5 | 5 | − |
| 23 | 3.2 | 5 | 5 | 5 | 5 | − |
| | 12.5 | 5 | 5 | 5 | 5 | − |
| 27 | 3.2 | 3 | 5 | 2 | 2 | − |
| | 12.5 | 4 | 5 | 3 | 3 | − |
| 29 | 0.8 | 5 | 5 | 4.5 | 5 | − |
| | 3.2 | 5 | 5 | 5 | 5 | − |
| 30 | 0.8 | 5 | 5 | 5 | 5 | − |
| | 3.2 | 5 | 5 | 5 | 5 | − |
| 34 | 0.8 | 5 | 5 | 4.5 | 5 | − |
| | 3.2 | 5 | 5 | 5 | 5 | − |
| 35 | 0.8 | 5 | 5 | 5 | 5 | − |
| | 3.2 | 5 | 5 | 5 | 5 | − |
| 37 | 0.8 | 5 | 5 | 4 | 5 | − |
| | 3.2 | 5 | 5 | 4.5 | 5 | − |
| 39 | 0.8 | 5 | 5 | 5 | 5 | − |
| | 3.2 | 5 | 5 | 5 | 5 | − |
| 41 | 0.8 | 5 | 5 | 5 | 5 | − |
| | 3.2 | 5 | 5 | 5 | 5 | − |
| 46 | 0.8 | 5 | 5 | 3 | 5 | − |
| | 3.2 | 5 | 5 | 5 | 5 | + |
| standard A | 12.5 | 5 | 5 | 0 | 0 | − |
| | 25.0 | 5 | 5 | 3 | 0 | + |
| standard B | 3.2 | 5 | 5 | 3 | 0 | + |
| | 6.4 | 5 | 5 | 4.5 | 0 | ++ | broadleaf(1): monochoria, toothcup, false pimpernel, water-wort standard CNP:

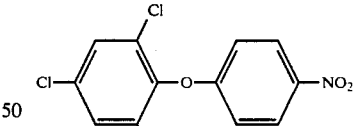

Standard A (CNP)

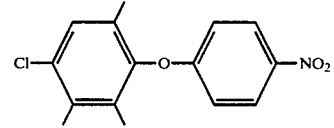

Standard B (oxadizon)

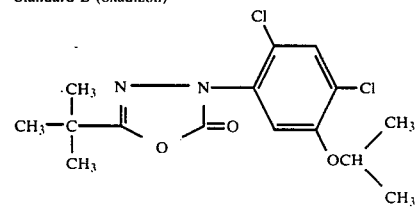

As are seen in the results of Test Example 1 shown in Table 2, every one of the tested present compounds showed an excellent herbicidal activity to annual and perennial weed and in addition, every one of the tested compounds was quite safe to the rice seedlings.

TEST EXAMPLE 2

Post-emergence treatment in flooded condition

A fixed amount of paddy field soil was filled in each Wagner pot sized 1/5,000 are to provide a condition similar to a paddy field and there are sown a fixed amount of seeds of barnyard grass, monochoria, toothcup, false pimpernal, water wort and bulrush.

In addition tubers of arrowhead were buried 1 cm under the surface of soil at a rate of 3 pieces per pot, three 2.5-leaf stage rice seedlings (variety: Nihonbare) were transplanted from a nursery, the pot was flooded with water 3 cm deep and then placed in a greenhouse.

When the weeds grew to reach 1- to 2-leaf stage, a diluted solution of the wettable powder of the compound of the present invention, was applied to the flood at a rate of 3.2 to 12.5 g of the active compound of the present invention per are.

After 30 days from the treatment with the diluted solution, the herbicidal activity was observed and obtained the results as shown in Table 3. The classification basis of the results is the same as in Test Example 1.

TABLE 3

| | | Post emergence treatment in flooded condition | | | |
|---|---|---|---|---|---|
| | | Herbicidal activity | | | Phyto- |
| Compound No. | Dosage g/a | barnyard grass | broad-leaf (1) | allow-head | bulrush | toxicity to rice |
| 14 | 3.2 | 5 | 5 | 5 | 5 | — |
| | 12.5 | 5 | 5 | 5 | 5 | + |
| 15 | 3.2 | 5 | 5 | 4 | 3 | — |
| | 12.5 | 5 | 5 | 4.5 | 4.5 | — |
| 17 | 3.2 | 5 | 5 | 4.5 | 5 | — |
| | 12.5 | 5 | 5 | 5 | 5 | + |
| 18 | 3.2 | 4 | 5 | 1 | 5 | — |
| | 12.5 | 5 | 5 | 4 | 5 | ++ |
| 19 | 3.2 | 4 | 5 | 2 | 3 | — |
| | 12.5 | 5 | 5 | 4 | 5 | + |
| 20 | 3.2 | 5 | 5 | 3 | 3 | — |
| | 12.5 | 5 | 5 | 4 | 5 | — |
| 21 | 3.2 | 5 | 5 | 4 | 5 | — |
| | 12.5 | 5 | 5 | 4 | 5 | + |
| 29 | 3.2 | 5 | 5 | 3 | 3 | — |
| | 12.5 | 5 | 5 | 4 | 4 | + |
| 30 | 3.2 | 5 | 5 | 5 | 5 | — |
| | 12.5 | 5 | 5 | 5 | 5 | + |
| 31 | 3.2 | 5 | 5 | 5 | 5 | — |
| | 12.5 | 5 | 5 | 5 | 5 | + |
| 39 | 3.2 | 5 | 5 | 4 | 5 | — |
| | 12.5 | 5 | 5 | 5 | 5 | — |
| 41 | 3.2 | 5 | 5 | 4.5 | 5 | — |
| | 12.5 | 5 | 5 | 5 | 5 | — |
| 46 | 3.2 | 5 | 5 | 3 | 4 | — |
| | 12.5 | 5 | 5 | 5 | 5 | — |
| Standard A | 12.5 | 3 | 5 | 0 | 0 | — |
| | 25.0 | 5 | 5 | 0 | 0 | + |

Standard A: the same as in Test example 1

As are seen in the results of Test Examples 1 and 2 shown in Tables 2 and 3, every one of the tested present compounds showed an excellent herbicidal activity to annual and perennial weeds in paddy fields in pre- and post-emergence treatments and in addition, every one of the tested present compounds was quite safe to the rice seedlings when applied to the soil pre-transplanting or post-transplanting.

Test examples in farm field are as follows:

TEST EXAMPLE 3

A fixed amount of field soil was filled in a round plastic case of 8 cm across and 8 cm deep, and a fixed amount of seeds of crabgrass, foxtail, pigweed and lamb's-quarters was sown followed by covering them with soil 0.5 to 1 cm thick. Then immediately a diluted solution of the compound of the present invention was applied to treat the whole surface of soil in case at a rate of 3.2 to 50 g of the active compound of the present invention per are.

After the treatment the cultivation was done in a greenhouse and the herbicidal activity was observed on the 20th day. The test was carried out on 2-replication system and each average value was sought. The judging standard of the results is the same as in Test Example 1. The test results are shown in Tables 4 and 4'.

TABLE 4'

| | | Pre-emergence soil surface treatment | | | |
|---|---|---|---|---|---|
| | | Herbicidal activity | | | |
| Compound No. | Dosage g/a | foxtail | crabgrass | pigweed | lamb's-quarters |
| 1 | 12.5 | 2 | 2 | 4 | 4.5 |
| | 50 | 3 | 3 | 5 | 5 |
| 2 | 12.5 | 5 | 5 | 5 | 5 |
| | 50 | 5 | 5 | 5 | 5 |
| 3 | 12.5 | 5 | 5 | 5 | 5 |
| | 50 | 5 | 5 | 5 | 5 |
| 5 | 12.5 | 5 | 5 | 5 | 5 |
| | 50 | 5 | 5 | 5 | 5 |
| 6 | 12.5 | 5 | 5 | 5 | 5 |
| | 50 | 5 | 5 | 5 | 5 |
| 7 | 12.5 | 5 | 5 | 5 | 5 |
| | 50 | 5 | 5 | 5 | 5 |
| standard Nitrofen | 12.5 | 2 | 3 | 5 | 5 |
| | 50 | 5 | 5 | 5 | 5 |
| not treated | — | 0 | 0 | 0 | 0 |
| 14 | 3.2 | 3 | 4 | 5 | 5 |
| | 12.5 | 5 | 5 | 5 | 5 |
| 15 | 3.2 | 2 | 3 | 5 | 5 |
| | 12.5 | 4 | 5 | 5 | 5 |
| 17 | 3.2 | 3.5 | 3 | 5 | 5 |
| | 12.5 | 5 | 5 | 5 | 5 |
| 19 | 3.2 | 1 | 1 | 5 | 5 |
| | 12.5 | 2 | 3 | 5 | 5 |
| 21 | 3.2 | 2 | 1 | 5 | 5 |
| | 12.5 | 4 | 3.5 | 5 | 5 |
| 22 | 3.2 | 2 | 3 | 5 | 5 |
| | 12.5 | 4.5 | 4 | 5 | 5 |
| 29 | 3.2 | 4 | 4 | 5 | 5 |
| | 12.5 | 4.5 | 5 | 5 | 5 |
| 32 | 3.2 | 3 | 3 | 5 | 5 |
| | 12.5 | 4 | 4 | 5 | 5 |
| 35 | 3.2 | 4 | 4 | 5 | 5 |
| | 12.5 | 4.5 | 5 | 5 | 5 |
| 39 | 3.2 | 4 | 4 | 5 | 5 |
| | 12.5 | 5 | 5 | 5 | 5 |
| 46 | 3.2 | 2 | 2 | 5 | 5 |
| | 12.5 | 3 | 3 | 5 | 5 |
| standard C | 3.2 | 1 | 2 | 3 | 2 |
| | 12.5 | 4 | 5 | 5 | 5 |

Standard Nitrofen

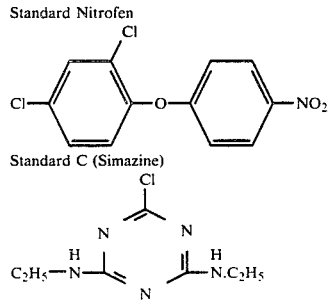

Standard C (Simazine)

TEST EXAMPLE 4

A fixed amount of field soil was filled in a plastic vessel sized 23 cm × 45 cm × 12.5 cm and a fixed amount of seeds of soybean, cotton, corn, wheat, sun flower and rice was sown followed by about 3 cm thick covering with soil.

Then immediately solution of the compound of the present invention was sprayed on the soil surface with a smaller sprayer at a rate of 12.5 to 50 g per are of the active compound of the present invention.

After the treatment the crops were grown in a greenhouse and 20 days later the degree of phytotoxicity against each crop was observed. The test was carried out on 2-replication system and each average value was sought.

The judging standard of test results is the same as in Test Example 1 and the results are shown in Table 5.

TABLE 5

Test example 4

| Compound No. | Dosage g/a | Phytotoxicity against crops | | | | | |
|---|---|---|---|---|---|---|---|
| | | soybean | cotton | corn | wheat | rice | sunflower |
| 1 | 12.5 | − | − | − | − | − | − |
| | 50 | − | − | + | + | − | − |
| 2 | 12.5 | − | − | − | − | − | − |
| | 50 | + | + | ++ | ++ | ++ | − |
| 3 | 12.5 | − | − | − | − | − | − |
| | 50 | − | − | − | − | − | − |
| 5 | 12.5 | − | − | − | − | − | − |
| | 50 | − | − | − | − | − | − |
| 6 | 12.5 | − | − | − | − | − | − |
| | 50 | − | − | − | − | − | − |
| 7 | 12.5 | − | − | − | − | − | − |
| | 50 | − | − | − | − | − | − |

| Compound No. | Dosage g/a | Phytotoxicity against crops | | |
|---|---|---|---|---|
| | | soybean | cotton | corn |
| 14 | 12.5 | − | − | − |
| | 50 | − | ++ | − |
| 15 | 12.5 | − | − | − |
| | 50 | − | ++ | − |
| 17 | 12.5 | − | − | − |
| | 50 | − | − | − |
| 19 | 12.5 | − | − | − |
| | 50 | − | − | − |
| 21 | 12.5 | − | − | − |
| | 50 | − | − | − |
| 22 | 12.5 | − | − | − |
| | 50 | − | − | − |
| 29 | 12.5 | − | − | − |
| | 50 | − | − | − |
| 32 | 12.5 | − | − | − |
| | 50 | − | − | − |
| 35 | 12.5 | − | − | − |
| | 50 | − | − | − |
| 39 | 12.5 | − | − | − |
| | 50 | − | − | − |
| 46 | 12.5 | − | − | − |
| | 50 | − | − | − |
| standard C | 12.5 | ++ | ++ | − |
| | 50 | +++ | +++ | ++ |

Standard C: the same as in Test example 3

TEST EXAMPLE 5

Post-emergence treatment

Into the soil of farm field in a plastic pot of 8 cm in diameter and 8 cm in depth, a predetermined amount of seeds of the following species of weeds in Table 7 was sown, and the pots were kept to grow the weeds. And when the weeds are in the 3 to 4 leaf stage, a liquid which had been prepared by diluting a wettable powder formulated using the compounds of Table 7 so as to apply 3.2 to 50 g of the present compound per 100 m² of the surface of the soil in the pot, was sprayed onto the weeds in the pot. The test was carried out on 2-replication system. After 20 days the herbicidal effect on the weeds was investigated, the extent of herbicidal effect being indexed according to the same criteria as the Test Example 1 and shown in Table 7.

TABLE 6

| Compound No. | Post-emergence treatment | | |
|---|---|---|---|
| | Dosage g/a | herbicidal activity | |
| | | foxtail | pigweed |
| 1 | 12.5 | 2 | 5 |
| | 50 | 3 | 5 |
| 2 | 12.5 | 2 | 5 |
| | 50 | 3 | 5 |
| 3 | 12.5 | 3 | 5 |
| | 50 | 4 | 5 |
| 5 | 12.5 | 4 | 5 |
| | 50 | 5 | 5 |
| 10 | 12.5 | 5 | 5 |
| | 50 | 5 | 5 |
| 11 | 12.5 | 2 | 5 |
| | 50 | 3 | 5 |
| not treated | — | 0 | 0 |
| 13 | 3.2 | 4 | 5 |
| | 12.5 | 4.5 | 5 |
| 14 | 3.2 | 4 | 5 |
| | 12.5 | 4.5 | 5 |
| 15 | 3.2 | 1 | 5 |
| | 12.5 | 4 | 5 |
| 16 | 3.2 | 4 | 5 |
| | 12.5 | 5 | 5 |
| 17 | 3.2 | 5 | 5 |
| | 12.5 | 5 | 5 |
| 19 | 3.2 | 4 | 5 |
| | 12.5 | 4.5 | 5 − |
| 21 | 3.2 | 4 | 5 |
| | 12.5 | 5 | 5 |
| 24 | 3.2 | 2 | 4 |
| | 12.5 | 3 | 4.5 |
| 29 | 3.2 | 4 | 5 |
| | 12.5 | 5 | 5 |
| 30 | 3.2 | 4 | 5 |
| | 12.5 | 5 | 5 |
| 34 | 3.2 | 4 | 5 |
| | 12.5 | 5 | 5 |
| 36 | 3.2 | 4 | 5 |
| | 12.5 | 5 | 5 |
| 37 | 3.2 | 5 | 5 |
| | 12.5 | 5 | 5 |
| 40 | 3.2 | 4 | 5 |
| | 12.5 | 5 | 5 |
| 42 | 3.2 | 4 | 5 |
| | 12.5 | 5 | 5 |
| 46 | 3.2 | 3 | 5 |
| | 12.5 | 4 | 5 |
| 48 | 3.2 | 5 | 5 |
| | 12.5 | 5 | 5 |
| standard | 3.2 | 3 | 5 |
| D | 12.5 | 5 | 5 |

Standard D

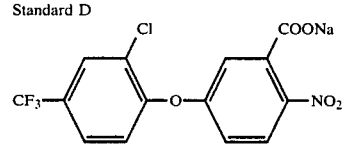

As are seen in the results of Test Examples 3 to 5, the present compound exhibits an excellent herbicidal activity on the major weeds on crop field in pre- and post-emergence treatments, and as are seen in the results of Test Example 4, the present compound does not harm the crop plants in the farm field and accordingly, the present compound can be suitably used as a herbicide in the ordinary farm field.

What we claim is:

1. A compound of the formula:

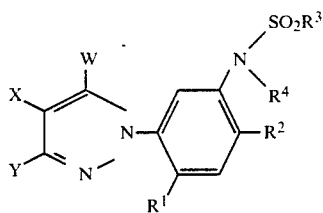

wherein $R^1$ is hydrogen, halogen or methyl, $R^2$ is hydrogen, halogen or lower alkyl, $R^3$ is lower alkyl which may be substituted by halogen or methylsulfonyl, benzyl, phenyl which may be substituted by halogen or nitro, $R^4$ is hydrogen; lower alkyl which may be substituted by carboxy or lower alkoxy carbonyl; lower alkenyl; lower alkynyl; methylsulfonyl or benzyl which may be substituted by halogen, X is hydrogen, halogen or $C_1$-$C_2$—alkyl, Y is $C_1$-$C_2$—alkyl, X may make—$(CH_2)_3$—or—$(CH_2)_4$—together with Y, W is halogen.

2. A compound according to claim 1 wherein $R^1$ is fluoro or chloro, $R^2$ is chloro or methyl, $R^3$ is lower alkyl, $R^4$ is methyl, ethyl, carboxymethyl or methoxy carbonyl methyl, X is chloro, Y is methyl or X makes —$(CH_2)_4$— together with Y, W is chloro.

3. A compound according to claim 1 wherein $R^1$ is fluoro, chloro or methyl, $R^2$ is chloro, bromo or methyl, $R^3$ is $CF_3$, $R^4$ is hydrogen, X is hydrogen, chloro, bromo or methyl, Y is methyl or X makes —$(CH_2)_4$— together with Y.

4. A compound according to claim 2 wherein $R^1$ is fluoro, $R^2$ is chloro, $R^3$ is methyl or ethyl, $R^4$ is methyl, carboxymethyl or methoxycarbonylmethyl, X is chloro, Y is methyl or X makes —$(CH_2)_4$— together with Y, W is chloro.

5. A compound according to claim 1 which is selected from the group consisting of:

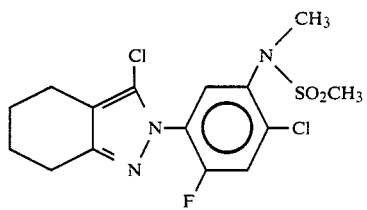

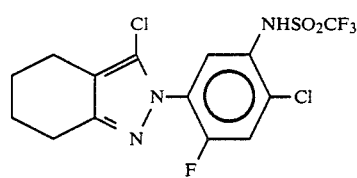

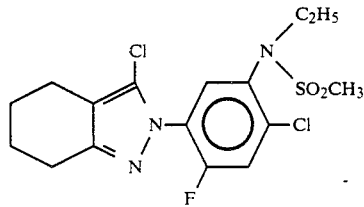

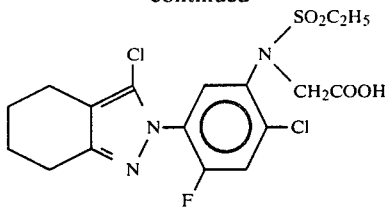

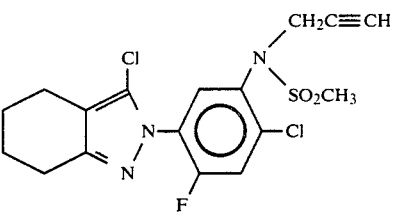

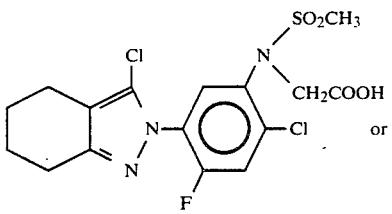

or

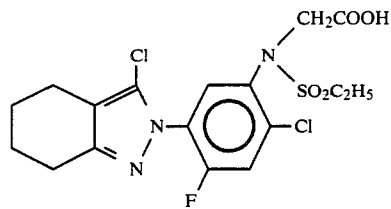

6. A herbicidal composition containing a herbicidally effective amount of a compound of the formula:

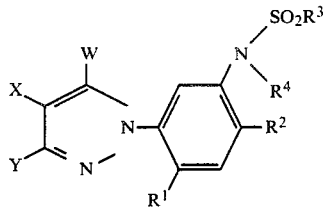

wherein $R^1$ is hydrogen, halogen or methyl, $R^2$ is hydrogen, halogen or lower alkyl, $R^3$ is lower alkyl which may be substituted by halogen or methylsulfonyl, benzyl, phenyl which may be substituted by halogen or nitro, $R^4$ is hydrogen; lower alkyl which may be substituted by carboxy or lower alkoxy carbonyl; lower alkenyl; lower alkynyl; methylsulfonyl or benzyl which may be substituted by halogen, X is hydrogen, halogen or $C_1$-$C_2$—alkyl, Y is $C_1$-$C_2$—alkyl, X may make a —$(CH_2)_3$— or —$(CH_2)_4$— together with Y, W is halogen and adjuvant(s).

7. A composition according to claim 6 wherein $R^1$ is fluoro or chloro, $R^2$ is chloro or methyl, $R^3$ is lower alkyl, $R^4$ is methyl, ethyl, carboxymethyl or methoxy carbonylmethyl, X is chloro, Y is methyl or X makes —$(CH_2)_4$— together with Y, W is chloro.

8. A composition according to claim 6 wherein $R^1$ is fluoro, chloro or methyl, $R^2$ is chloro, bromo or methyl, $R^3$ is $CF_3$, $R^4$ is hydrogen, X is hydrogen, chloro, bromo or methyl, Y is methyl or X makes —(CH₂)₄— together with Y.

9. A composition according to claim 7 wherein R¹ is fluoro, R² is chloro, R³ is methyl or ethyl, R⁴ is methyl, carboxymethyl or methoxycarbonylmethyl, X is chloro, Y is methyl or X makes —(CH₂)₄— together with Y, W is chloro.

10. A composition according to claim 6 wherein the effective component is selected from the group consisting of:

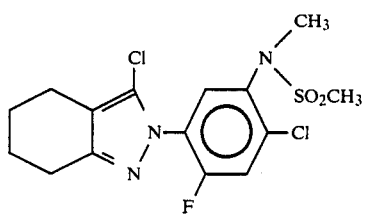

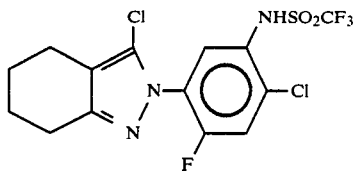

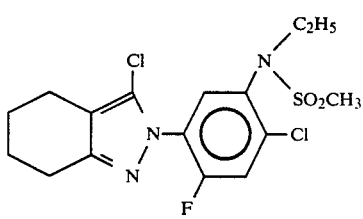

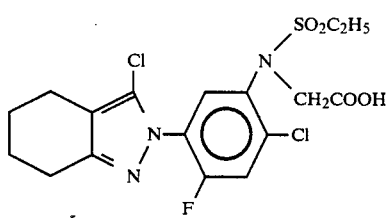

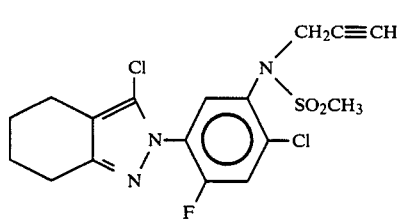

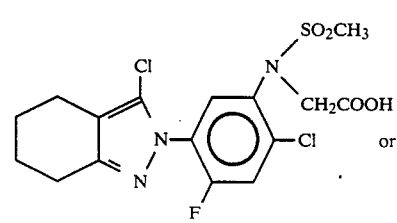 or

-continued

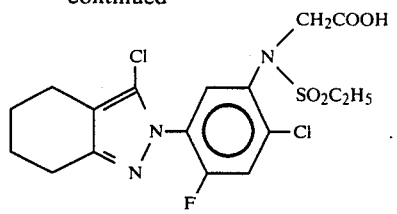

11. A method for killing weeds which comprises applying the weeds or locus thereof a herbicidally effective amount of the formula:

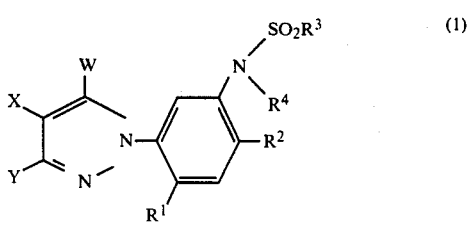

wherein R¹ is hydrogen, halogen or methyl, R² is hydrogen, halogen or lower alkyl, R³ is lower alkyl which may be substituted by halogen or methylsulfonyl, benzyl, phenyl which may be substituted by halogen or nitro, R⁴ is hydrogen; lower alkyl which may be substituted by carboxy or lower alkoxy carbonyl; lower alkenyl; lower alkynyl; methylsulfonyl or benzyl which may be substituted by halogen, X is hydrogen, halogen or C₁-C₂—alkyl, Y is C₁-C₂—alkyl, X may make a —(CH₂)₃— or —(CH₂)₄— together with Y, W is halogen.

12. A method according to claim 11 wherein R¹ is fluoro or chloro, R² is chloro or methyl, R³ is lower alkyl, R⁴ is methyl, ethyl, carboxymethyl or methoxycarbonylmethyl, X is chloro, Y is methyl or X makes —(CH₂)₄— together with Y, W is chloro.

13. A method according to claim 11 wherein R¹ is fluoro, chloro or methyl, R² is chloro, bromo or methyl, R³ is CF₃, R⁴ is hydrogen, X is hydrogen, chloro, bromo or methyl, Y is methyl or X makes —(CH₂)₄— together with Y.

14. A compound according to claim 12 wherein R¹ is fluoro, R² is chloro, R³ is methyl or ethyl, R⁴ is methyl, carboxymethyl or methoxycarbonylmethyl, X is chloro, Y is methyl or X makes —(CH₂)₄— together with Y, W is chloro.

15. A method according to claim 11 wherein effective component is selected from the group consisting of:

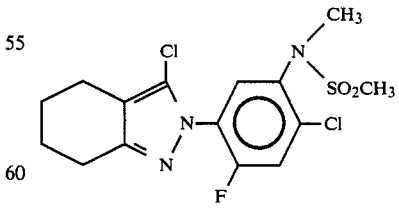

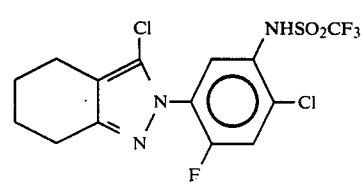

-continued
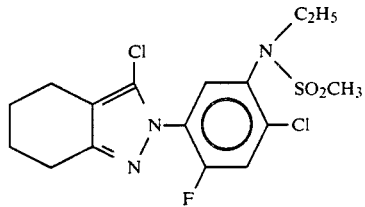
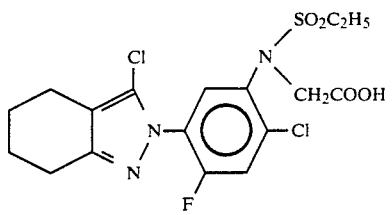
-continued
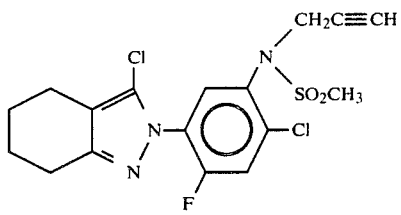
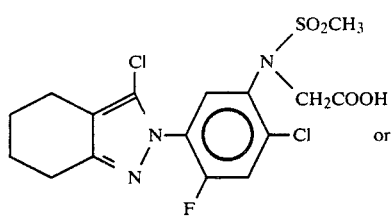 or
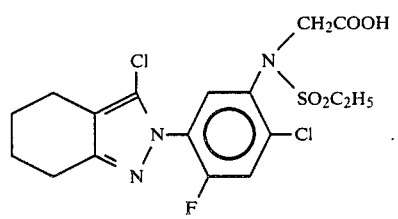
* * * * *